United States Patent
Samson et al.

[11] Patent Number: 6,143,013
[45] Date of Patent: *Nov. 7, 2000

[54] HIGH PERFORMANCE BRAIDED CATHETER

[75] Inventors: Gene Samson, Milpitas; Uriel Hiram Chee, San Carlos; Kim Nguyen; Edward J. Snyder, both of San Jose; Erik T. Engelson, Menlo Park, all of Calif.

[73] Assignee: Target Therapeutics, Inc., Fremont, Calif.

[ * ] Notice: This patent issued on a continued prosecution application filed under 37 CFR 1.53(d), and is subject to the twenty year patent term provisions of 35 U.S.C. 154(a)(2).

[21] Appl. No.: 08/641,259

[22] Filed: Apr. 30, 1996

Related U.S. Application Data

[63] Continuation-in-part of application No. 08/430,445, Apr. 28, 1995, and a continuation-in-part of application No. 08/521,671, Aug. 31, 1995.

[51] Int. Cl.⁷ .................................................. A61M 29/00
[52] U.S. Cl. .......................................... 606/192; 604/264
[58] Field of Search ................................... 604/264, 280, 604/282; 606/191–195

[56] References Cited

U.S. PATENT DOCUMENTS

| | | |
|---|---|---|
| 243,396 | 6/1881 | Pfarre . |
| 2,211,975 | 8/1940 | Hendrickson . |
| 2,437,542 | 3/1948 | Krippendorf . |
| 3,174,851 | 3/1965 | Buehler et al. . |
| 3,416,531 | 12/1968 | Edwards . |
| 3,753,700 | 8/1973 | Harrison et al. . |
| 3,757,768 | 9/1973 | Kline . |
| 3,924,632 | 12/1975 | Cook . |
| 4,425,919 | 1/1984 | Alston, Jr. et al. . |

(List continued on next page.)

FOREIGN PATENT DOCUMENTS

| | | |
|---|---|---|
| 0098100 | 1/1984 | European Pat. Off. . |
| 0420993 | 4/1991 | European Pat. Off. . |
| 0421650 | 4/1991 | European Pat. Off. . |
| 0594201 | 4/1994 | European Pat. Off. . |
| 0643979 | 3/1995 | European Pat. Off. . |

(List continued on next page.)

*Primary Examiner*—Michael Buiz
*Assistant Examiner*—Len Ngo
*Attorney, Agent, or Firm*—Morrison & Foerster LLP

[57] ABSTRACT

This is a catheter assembly and a section of that catheter assembly. That catheter assembly may be used in accessing a tissue target within the body, typically a target which is accessible through the vascular system. Central to the invention is the use of a braided metallic reinforcing member, typically of super-elastic alloy ribbon, situated within the catheter body in such a way to create a catheter having an exceptionally thin wall, controlled stiffness, high resistance to kinking, and complete recovery in vivo from kinking situations. The braid may have a single pitch or may vary in pitch along the axis of the catheter or catheter section. The braided ribbon reinforcing member typically is placed between a flexible outer tubing member and an inner tubing member to produce a catheter section which is very flexible but highly kink resistant. The catheter sections made according to this invention may be used alone or in conjunction with other catheter sections either made using the concepts shown herein or made in other ways. The more proximal sections of the catheter assembly are often substantially stiffer than the more distal sections due to the presence of stiff polymeric tubing or metallic tubing or composited materials in the stiffer section.

35 Claims, 10 Drawing Sheets

U.S. PATENT DOCUMENTS

| | | |
|---|---|---|
| 4,430,083 | 2/1984 | Ganz et al. . |
| 4,484,586 | 11/1984 | McMickle et al. . |
| 4,516,972 | 5/1985 | Samson . |
| 4,657,024 | 4/1987 | Coneys . |
| 4,676,229 | 6/1987 | Krasnicki et al. . |
| 4,737,153 | 4/1988 | Shimamura et al. . |
| 4,739,768 | 4/1988 | Engelson . |
| 4,806,182 | 2/1989 | Rydell et al. . |
| 4,832,681 | 5/1989 | Lenck . |
| 4,899,787 | 2/1990 | Ouchi et al. . |
| 4,981,478 | 1/1991 | Evard et al. . |
| 4,985,022 | 1/1991 | Fearnot et al. . |
| 4,994,069 | 2/1991 | Ritchart et al. . |
| 5,037,404 | 8/1991 | Gold et al. . |
| 5,057,092 | 10/1991 | Webster, Jr. . |
| 5,069,674 | 12/1991 | Fearnot et al. . |
| 5,122,136 | 6/1992 | Guglielmi et al. . |
| 5,176,660 | 1/1993 | Truckai . |
| 5,178,158 | 1/1993 | de Toledo . |
| 5,180,376 | 1/1993 | Fischell . |
| 5,184,627 | 2/1993 | de Toledo . |
| 5,217,482 | 6/1993 | Keith . |
| 5,222,949 | 6/1993 | Kaldany . |
| 5,234,416 | 8/1993 | Macaulay ............................... 604/282 |
| 5,248,305 | 9/1993 | Zdrahala . |
| 5,279,596 | 1/1994 | Castaneda et al. . |
| 5,313,967 | 5/1994 | Lieber et al. . |
| 5,336,205 | 8/1994 | Zenzen et al. . |
| 5,354,295 | 10/1994 | Guglielmi et al. . |
| 5,356,388 | 10/1994 | Sepetka et al. ......................... 604/164 |
| 5,405,338 | 4/1995 | Kranys . |
| 5,454,795 | 10/1995 | Samson . |
| 5,531,715 | 7/1996 | Engelson et al. . |
| 5,533,987 | 7/1996 | Pray et al. .............................. 604/280 |
| 5,538,512 | 7/1996 | Zenzen et al. . |
| 5,538,513 | 7/1996 | Okajima .................................. 604/282 |
| 5,591,142 | 1/1997 | Van Erp .................................. 604/282 |

FOREIGN PATENT DOCUMENTS

| | | |
|---|---|---|
| 2613231 | 10/1988 | France . |
| 3242449 | 5/1983 | Germany . |
| 3642107 | 6/1987 | Germany . |
| 2-283346 | 11/1990 | Japan . |
| 3-023830 | 1/1991 | Japan . |
| 5-056910 | 3/1993 | Japan . |
| 5-220225 | 8/1993 | Japan . |
| WO 92/07507 | 5/1992 | WIPO . |
| WO 93/05842 | 4/1993 | WIPO . |
| WO 93/15785 | 8/1993 | WIPO . |
| WO 95/13110 | 5/1995 | WIPO . |

HIGH PERFORMANCE BRAIDED CATHETER

RELATED APPLICATION

This is a continuation-in-part of U.S. patent application Ser. No. 08/430,445, filed Apr. 28, 1995, and also a continuation-in-part of U.S. patent application Ser. No. 08/521,671, filed Aug. 31, 1995, the entirety of which are incorporated by reference.

FIELD OF THE INVENTION

This invention is a surgical device. In particular, it is a catheter assembly and a section of that catheter assembly. That catheter assembly may be used in accessing a tissue target within the body, typically a target which is accessible through the vascular system. Central to the invention is the use of a braided metallic reinforcing member, typically of super-elastic alloy ribbon, situated within the catheter body in such a way to create a catheter section having an exceptionally thin wall, controlled stiffness, high resistance to kinking, and complete recovery in vivo from kinking situations. The braid may have a single pitch or may vary in pitch along the axis of the catheter or catheter section. The braided ribbon reinforcing member typically is placed between a flexible outer tubing member and an inner tubing member to produce a catheter section which is very flexible but highly kink resistant.

The catheter sections made according to this invention may be used alone or in conjunction with other catheter sections either made using the concepts shown herein or made in other ways. The more proximal sections of the catheter assembly are often substantially stiffer than the more distal sections due to the presence of stiff polymeric tubing or metallic tubing or composited materials in the stiffer section.

BACKGROUND OF THE INVENTION

Catheters are increasingly used to access remote regions of the human body and, in doing so, delivering diagnostic or therapeutic agents to those sites. In particular, catheters which use the circulatory system as the pathway to these treatment sites are especially practical. Catheters are also used to access other regions of the body, e.g., genito-urinary regions, for a variety of therapeutic and diagnostic reasons. One such treatment of diseases of the circulatory system is via angioplasty (PCA). Such a procedure uses catheters having balloons on their distal tips. It is similarly common that those catheters are used to deliver a radio-opaque agent to the site in question prior to the PCA procedure to view the problem prior to treatment.

Often the target which one desires to access by catheter is within a soft tissue such as the liver or the brain. These are difficult sites to reach. The catheter must be introduced through a large artery such as those found in the groin or in the neck and then be passed through ever-narrower regions of the arterial system until the catheter reaches the selected site. Often such pathways will wind back upon themselves in a multi-looped path. These catheters are difficult to design and to utilize in that they must be fairly stiff at their proximal end so to allow the pushing and manipulation of the catheter as it progresses through the body, and yet must be sufficiently flexible at the distal end to allow passage of the catheter tip through the loops and increasingly smaller blood vessels mentioned above and yet at the same time not cause significant trauma to the blood vessel or to the surrounding tissue. Further details on the problems and an early, but yet effective, way of designing a catheter for such a traversal may be found in U.S. Pat. No. 4,739,768, to Engelson. These catheters are designed to be used with a guidewire. A guidewire is simply a wire, typically of very sophisticated design, which is the "scout" for the catheter. The catheter fits over and slides along the guidewire as it passes through the vasculature. Said another way, the guidewire is used to select the proper path through the vasculature with the urging of the attending physician and the catheter slides along behind once the proper path is established.

There are other ways of causing a catheter to proceed through the human vasculature to a selected site, but a guidewire-aided catheter is considered to be both quite quick and somewhat more accurate than the other procedures. One such alternative procedure is the use of a flow-directed catheter. These devices often have a small balloon situated on the distal end of the catheter which may be alternately deflated and inflated as the need to select a route for the catheter is encountered.

This invention is an adaptable one and may be used in a variety of catheter formats. The invention utilizes the concept of combining one or more polymeric tubes with a metallic braid comprising ribbons of a super-elastic alloy. The construction technique has the benefit of producing catheter sections having small overall diameters but with exceptional strength, resistance to kinking, and recovery from kinking (even in vivo) should such kinking occur. This catheter may be used in conjunction with a guidewire, but the catheter body may also be used as a flow-directed catheter with the attachment of a balloon or in combination with a specifically flexible tip, as is seen, for instance, in U.S. Pat. No. 5,336,205 to Zenzen et al., the entirety of which is incorporated by reference.

The use of braids in a catheter body is not a novel concept. Typical background patents are discussed below. However, none of these documents have used our concept to produce a catheter which has the physical capabilities of the catheter of this invention.

Multi-Wrap Catheters

There are a number of catheters discussed in the literature which utilize catheter bodies having multiply-wrapped reinforcing material. These catheters include structures having braided bands or ones in which the spirally wound material is simply wound in one direction and the following layer or layers are wound in the other.

Crippendorf, U.S. Pat. No. 2,437,542, describes a "catheter-type instrument" which is typically used as a ureteral or urethral catheter. The physical design is said to be one having a distal section of greater flexibility and a proximal section of lesser flexibility. The device is made of intertwined threads of silk, cotton, or some synthetic fiber. It is made by impregnating a fabric-based tube with a stiffening medium which renders the tube stiff yet flexible. The thus-plasticized tubing is then dipped in some other medium to allow the formation of a flexible varnish-like layer. This latter material may be a tung oil base or a phenolic resin and a suitable plasticizer. There is no indication that this device is of the flexibility described herein. Additionally, it appears to be the type which is used in some region other than in the body's periphery or in its soft tissues.

Similarly, U.S. Pat. No. 3,416,531, to Edwards, shows a catheter having braiding-edge walls. The device further has additional layers of other polymers such as TEFLON and the like. The strands found in the braiding in the walls appear to be threads having circular cross-sections. There is no suggestion of constructing a device using ribbon materials. Furthermore, the device is shown to be fairly stiff in that it is designed so that it may be bent using a fairly large handle at its proximal end.

U.S. Pat. No. 3,924,632, to Cook, shows a catheter body utilizing fiberglass bands wrapped spirally for the length of the catheter. As is shown in FIG. 2 and the explanation of the Figure at column 3, lines 12 and following, the catheter uses fiberglass bands which are braided, that is to say, bands which are spiraled in one direction cross over and under bands which are spiraled in the opposite direction. Additionally, it should be observed that FIG. 3 depicts a catheter shaft having both an inner lining or core 30 and an outer tube 35.

U.S. Pat. No. 4,425,919, to Alston, Jr. et al., shows a multilayered catheter assembly using multi-stranded flat wire braid. The braid 14 in FIG. 3 further covers an interior tubing or substrate 12.

U.S. Pat. No. 4,484,586 shows a method for the production of a hollow, conductive medical tubing. The conductive wires are placed in the walls of hollow tubing specifically for implantation in the human body, particularly for pacemaker leads. The tubing is preferably made of an annealed copper wire which has been coated with a body-compatible polymer such as a polyurethane or a silicone. After coating, the copper wire is wound into a tube. The wound substrate is then coated with still another polymer to produce a tubing having spiral conducting wires in its wall.

A document showing the use of a helically wound ribbon of flexible material in a catheter is U.S. Pat. No. 4,516,972, to Samson. This device is a guiding catheter and it may be produced from one or more wound ribbons. The preferred ribbon is a polyaramid material known as Kevlar 49. Again, this device is a device which must be fairly stiff. It is a device which is designed to take a "set" and remain in a particular configuration as another catheter is passed through it. It must be soft enough so as not to cause substantial trauma, but it is certainly not for use with a guidewire. It would not meet the flexibility criteria required of the inventive catheter described herein.

U.S. Pat. No. 4,806,182, to Rydell et al, shows a device using a stainless steel braid imbedded in its wall and having an inner layer of a polyfluorocarbon. The process also described therein is a way to laminate the polyfluorocarbon to a polyurethane inner layer so as to prevent delamination.

U.S. Pat. No. 4,832,681, to Lenck, shows a method and apparatus useful for artificial fertilization. The device itself is a long portion of tubing which, depending upon its specific materials of construction, may be made somewhat stiffer by the addition of a spiral reinforcement comprising stainless steel wire.

U.S. Pat. No. 4,981,478, to Evard et al., discloses a multi-sectioned or composite vascular catheter. The interior section of the catheter appears to have three sections making up the shaft. The most interior (and distal) section, 47, appears to be a pair of coils 13 and 24 having a polymeric tubing member 21 placed within it. The next, more proximal, section is 41, and FIG. 4 shows it to be "wrapped or braided" about the next inner layer discussed just above. The drawing does not show it to be braided but, instead, a series of spirally wrapped individual strands. Finally, the outermost tubular section of this catheter core is another fiber layer 49, of similar construction to the middle section 26 discussed just above.

Another catheter showing the use of braided wire is shown in U.S. Pat. No. 5,037,404, to Gold et al. Mention is made in Gold et al of the concept of varying the pitch angle between wound strands so to result in a device having differing flexibilities at differing portions of the device. The differing flexibilities are caused by the difference in pitch angle. No mention is made of the use of ribbon, nor is any specific mention made of the particular uses to which the Gold et al. device may be placed.

U.S. Pat. No. 5,057,092, to Webster, Jr., shows a catheter device used to monitor cardiovascular electrical activity or to electrically stimulate the heart. The catheter uses braided helical members having a high modulus of elasticity, e.g., stainless steel. The braid is a fairly complicated, multi-component pattern shown very well in FIG. 2.

U.S. Pat. No. 5,176,660 shows the production of catheters having reinforcing strands in their sheath wall. The metallic strands are wound throughout the tubular sheath in a helical crossing pattern so to produce a substantially stronger sheath. The reinforcing filaments are used to increase the longitudinal stiffness of the catheter for good "pushability". The device appears to be quite strong and is wound at a tension of about 250,000 lb./in.$^2$ or more. The flat strands themselves are said to have a width of between 0.006 and 0.020 inches and a thickness of 0.0015 and 0.004 inches. There is no suggestion to use these concepts in devices having the flexibility and other configurations described below.

Another variation which utilizes a catheter wall having helically placed liquid crystal fibrils is found in U.S. Pat. No. 5,248,305, to Zdrahala. The catheter body is extruded through an annular die, having relatively rotating inner and outer mandrel dies. In this way, the tube containing the liquid crystal polymer plastic-containing material exhibits a bit of circumferential orientation due to the rotating die parts. At column 2, line 40 and following, the patent suggests that the rotation rate of the inner and outer walls of the die may be varied as the tube is extruded, with the result that various sections of the extruded tube exhibit differing stiffnesses.

U.S. Pat. No. 5,217,482 shows a balloon catheter having a stainless steel hypotube catheter shaft and a distal balloon. Certain sections of the device shown in the patent use a spiral ribbon of stainless steel secured to the outer sleeve by a suitable adhesive to act as a transition section from a section of very high stiffness to a section of comparatively low stiffness.

Japanese Kokai 05-220,225, owned by the Terumo Corporation, describes a catheter in which the torsional rigidity of the main body is varied by incorporating onto an inner tubular section 33, a wire layer which is tightly knitted at the proximal section of the catheter and more loosely knitted at a midsection.

Single-Layer, Reinforced Catheters

There are a variety of catheters which, unlike the devices discussed above, utilize but a single layer of reinforcing material.

For instance, U.S. Pat. No. 243,396 to Pfarre, patented in June of 1881, shows the use of a surgical tube having a wire helix situated within the tube wall. The wire helix is said to be vulcanized into the cover of the device.

U.S. Pat. No. 2,211,975, to Hendrickson, shows a similar device also comprising a stainless steel wire 15 embedded in the inner wall of a rubber catheter.

U.S. Pat. No. 3,757,768, to de Toledo, shows a "unitary, combined spring guide-catheter that includes an inner wall portion formed as a continuous helical spring with the helices in contact with each other and an outer wall portion formed from an inert plastic material enclosing the spring in such a manner as to become firmly bonded to the spring while having its outer surface smooth". There is no suggestion to separate the windings of the coil in any fashion.

U.S. Pat. No. 4,430,083 describes a catheter used for percutaneous administration of a thrombolytic agent directly to a clot in a coronary artery. The device itself is an elongated, flexible tube supported by helically wound wire having a specific cross-sectional shape. The wire is wound into a series of tight, contiguous coils to allow heat shrinking of tubing onto the outside of the wire of the shape of the outer surface of the wire as wound into the helix provides the heat-shrunk tubing with footing for a tight fit.

U.S. Pat. No. 4,567,024, to Coneys, shows a catheter which employs a set of helical strips within the wall of the catheter. However, the helical strips are of a radio-opaque material, e.g., fluorinated ethylene-propylene. It is not clear that the blended radio-opaque material necessarily provides any physical benefit other than the ability to allow the catheter shaft to be seen when viewed with a fluoroscope.

U.S. Pat. No. 4,737,153, to Shimamura et al., describes a device which is characterized as a "reinforced therapeutic tube" and which uses a spiral reinforcing material embedded within the wall of the device.

U.S. Pat. No. 5,069,674, to Fearnot et al. (and its parent, U.S. Pat. No. 4,985,022), shows a small diameter epidural catheter having a distal tip made up of a stainless steel wire which is helically wound and placed within a tubular sheath or tube. There is no suggestion within the patent that the interior coil be made to adhere to the outer tubular sheath.

Similarly, U.S. Pat. No. 5,178,158, to de Toledo, shows what is characterized as a "convertible wire for use as a guidewire or catheter". The patent describes a structure which comprises an interior wire or spring section shown, in the drawings, to be of generally rectangular cross-section. Outer layers of the device include a polyamide sheath placed adjacent to the helical coil at the proximal end of the catheter (see column 4, lines 64 and following). The device also comprises an outer sheath 40 of Teflon that extends from the proximal end 12 to the distal end 14 of the device. The overlying sheath 40 may extend or overhang at the proximal or the distal end of the catheter. The distal tip portion 13 is said to be "flexible, soft, and floppy". The PCT Published Application corresponding to this patent is WO 92/07507.

U.S. Pat. No. 5,184,627 shows a guidewire suitable for infusion of medicaments to various sites along the guidewire. The guidewire is made up of a helically wound coil having a polyamide sheath enclosing its proximal portion and a Teflon sheath tightly covering the entire wire coil. The coil is closed at its distal end. There is no suggestion that the wire forming the helical core be adhesively attached to its outer coverings.

U.S. Pat. No. 5,313,967, to Lieber et al., shows a medical device, a portion of which is a helical coil which apparently may include an outer plastic sheath in some variations. Apparently, a secondary helix of a somewhat similar design (in that it is formed by rotating a flat wire or the like along its longitudinal axis to form a screw-like configuration) is included within the helical coil to provide axial pushability and torque transmission.

U.S. Pat. No. 5,405,338, to Kranys, describes a helically wound catheter incorporating a shaft component having a helically wound coil with a skin or webbing supported by the coil. The skin or webbing is said to contribute "negligibly to the resistance of the catheter to axially directed compressive forces. . . . " The catheter may include an inner, taut skin component.

The PCT application, WO 93/15785, to Sutton et al., describes kink-resistant tubing made up of a thin layer of an encapsulating material and a reinforcing coil. As is shown in the drawings, the supporting material is embedded within the wall of the tubing in each instance.

The PCT application bearing the number WO 93/05842, to Shin et al., shows a ribbon-wrapped catheter. The device is shown as a section of a dilatation catheter. The inner section 34 is a helically wound coil and is preferably a flat wire. See, page 6, lines 25 and following. The coil is then wrapped with a heat-shrunk jacket 34 formed of low-density polyethylene. A lubricious material such as a silicone coating may then be placed on the inner surface of the spring coil to "enhance handling of the guidewire". It is also said, on page 6 of the document, that the "entire spring coil, before it is wound or jacketed, may be coated with other materials such as Teflon to enhance lubricity or provide other advantages. In some embodiments, the spring coil has been plated with gold."

Endoscope Structures

Various endoscopic structures, used primarily in sizes which are larger than endovascular catheters utilize structures including stiffener materials.

U.S. Pat. No. 4,676,229, to Krasnicki et al., describes an endoscopic structure 30 having an ultra-thin walled tubular substrate 31 formed of a lubricious material such as TEFLON. The structure contains a filament supported substrate. The filament is coated with and embedded into a filler material, typically an elastomeric material. A highly lubricious outer coating 35, all as shown in FIG. 2, forms the outer layer of the device. FIG. 3 in Krasnicki et al., describes another variation of the endoscopic device in which a different selection of polymer tubing is utilized but the placement of the filamentary support remains varied in an intermediate material of an elastomer. In some variations of the device, the filament is strongly bonded to the inner tubular substrate using an adhesive 37 "such as an epoxy cement having sufficient bond strength to hold the filament to the substrate as it is deformed into a tight radius." See, column 3, lines 50 and following.

U.S. Pat. No. 4,899,787, to Ouchi et al. (and its foreign relative, German Offenlegungshrifft DE-3242449) describes a flexible tube for use in an endoscope having a flexible, basic tubular core structure made up of three parts. The three parts are an outer meshwork tube, an intermediate thermoplastic resin tube bonded to the outer meshwork tube, and an inner ribbon made of a stainless steel or the like which is adherent to the two polymeric and meshwork tubes such that the resin tube maintains an adherent compressive pressure in the finished flexible tube. The patent also suggests the production of an endoscope tube having "flexibility which varies in step-wise manner from one end of the tube to the other . . . [and is produced] by integrally bonding two or more thermoplastic resin tube sections formed of respective resin materials having different hardnesses to the outer surface of the tubular core structure . . .". See, column 2, lines 48 and following.

U.S. Pat. No. 5,180,376 describes an introducer sheath utilizing a thin, flat wire metal coil surrounded only on its exterior surface with a plastic tube of coating. The flat wire coil is placed there to lower the "resistance of the sheath to buckling while minimizing the wall thickness of the sheath." A variation using two counter-wound metal ribbons is also described.

European Patent Application 0,098,100 describes a flexible tube for an endoscope which uses a helically wound metallic strip having a braided covering contiguous to the outer surface of the coil and having still further out a polymeric coating 9. Interior to the coil is a pair of slender flexible sheaths which are secured to a "front-end piece 10" by soldering.

Japanese Kokai 2-283,346, describes a flexible endoscope tube. The tubular outer shell is made up of two layers of a high molecular weight laminated material. The tube also has an inner layer of an elastic material and interior to it all is a metallic ribbon providing stiffening.

Japanese Kokai 03-023830, also shows the skin for flexible tube used in an endoscope which is made up of a braid 3 prepared by knitting a fine wire of a metal with a flexible portion 2 which is prepared by spirally winding an elastic belt sheet-like material and a skin 4 with which the whole outer surface of the device is covered. The document appears to emphasize the use of a particular polyester elastomer.

Japanese Kokai 5-56,910, appears to show a multi-layered endoscope tube made up of layers of the spiral wound metallic ribbon covered by a polymeric sheath.

French Patent Document 2,613,231, describes a medical probe used with an endoscope or for some other device used to stimulate the heart. The device appears to be a helix having a spacing between 0 and 0.25 mm (See page 4, line 20) preferably rectangular in cross section (See Page 4, Line 1) and of a multi-phase alloy such as M35N, SYNTACOBEN, or ELGELOY (See Page 4).

German Offenlegungshrifft DE-3642107 describes an endoscope tube, formed of a spiral tube, a braid formed of fibers interwoven into a net (which braid is fitted on the outer peripheral surface of the spiral tube), and a sheath covering the outer peripheral surface of the braid.

None of the noted devices have the structure required by the claims recited herein.

Other Anti-kinking Configurations

U.S. Pat. No. 5,222,949, to Kaldany, describes a tube in which a number of circumferential bands are placed at regular intervals along a catheter shaft. The bands may be integrated into the wall of the catheter. A variety of methods for producing the bands in the tubular wall are discussed. These methods include periodically irradiating the wall to produce bands of a higher integral of cross-linking.

European Patent Application No. 0,421,650-A1 describes a method for producing a catheter from a roll of polymer film while incorporating other materials such as tinfoil elements or the like.

None of the documents cited above provides a structure required by the disclosure and claims recited below, particularly when the flexibility and ability to resist kinks is factored into the physical description of the devices.

SUMMARY OF THE INVENTION

This invention includes a catheter section made up of an inner liner and an outer covering and having a super-elastic alloy ribbon braid located between the liner and the covering. The inner liner may be of a polymeric composition. The inner liner and the outer covering, should they be adjacent the braid and both polymeric, may be selected from polymers which are melt-compatible or melt-miscible with each other. In this way, adjacent polymeric layers hold fast to the braid located between them. Such a combination of polymers although desirable is not critical to the inventive concept. The inner liner may also be a helical coil of ribbon or wire.

The super-elastic alloy braid is, in its most basic form, a braid comprising a number of small super-elastic alloy ribbons wound and treated in such a way that the resulting braid is dimensionally stable and the braided ribbons do not twist. The more basic forms of braids used in this invention include those which are made up of an even number of equally sized ribbons. Half of the ribbons are woven in a clockwise direction (as viewed along the axis of the braid) and the remaining half of the ribbons are woven in a counterclockwise direction. The various ribbons may, of course, be of differing size but the sum of the ribbons used in a particular direction should equal those wound in the other direction. Any imbalance will typically cause a helical curl in the resulting catheter. The super-elastic alloy of choice is one known generically as nitinol. Nitinol is an alloy of nickel and titanium which is blended and heat treated in if produce an alloy having exceptional resistance to plastic deformation upon physical strain. In addition to nickel and titanium, preferred compositions of the alloy may contain a modest amount, up to about 5%, or up to about 8%, of an iron group metal. Especially desired are ternary alloys containing at least about 1.5% (wt) of one or more alloying members selected from the group consisting of vanadium, chromium, manganese, iron, and cobalt, and particularly chromium or iron. The catheter section may additionally have other various layers of polymeric covering and liners as well as metallic tubing members desirably of braid or helical coils. Especially preferred liners comprise polytetrafluoroethylene (TFE) polymer. Hydrophilic coatings both on the interior and exterior are additionally contemplated.

The kink resistance of the catheter section is due to the presence and composition of the braid in cooperation with the tightly held polymers. In addition to exceptional kink resistance, the catheter section may be made in such a way that the wall is extraordinarily thin, particularly when compared to walls of catheters having equal strength but made solely of polymeric materials. The catheter section additionally is very resilient in that, unlike virtually any other commercial catheter, should the catheter section be kinked, the kink is self-healing. This resiliency means that the catheter need not be withdrawn from a patient's vasculature simply because the catheter has inadvertently kinked. Simple movement of the catheter will cure the kink. Kinking minimization is a matter of concern with many catheters in the marketplace today.

This invention additionally includes catheter sections with braids having more than one pitch or diameter or braid density in a section. The stiffness of the catheter section may be varied continuously by continuously varying the pitch or in a stepwise fashion by stepwise varying the pitch. The pitch may be varied during production of the braid or by changing the diameter of the braid after production. The braid may be partially constructed of polymeric fibers or carbon fibers either replacing a portion of the metallic ribbons or polymeric materials or placed in conjunction with a ribbon in the braid. Other metals, e.g., noble metals such as members of the platinum group or gold, may be used in the braid itself in much the same way to impart radio-opacity to the braid. To tailor the stiffness of the braid, the braid may first wound and portions of the ribbon then removed.

The catheter section of this invention may be used as a catheter assembly by itself—obviously in conjunction with such necessary and ancillary components as a Luerlock and some manner of providing radio-opacity to the catheter. The catheter section of this invention may be used in nose-to-tail configuration with other catheter sections of similar configuration or with catheter sections made in some other fashion.

The catheter section may be used in a catheter assembly having at least a.) a more distal section made up preferably of an inner liner and an outer covering and having a super-elastic alloy braid located between the liner and interior to the outer covering and b.) a more proximal section comprising a stiff polymeric or metallic tubing member, possibly with an inner lubricious liner. Other sections of these or other designs may be placed variously between the noted sections or distal of the distal braided section noted above.

DESCRIPTION OF THE INVENTION

This invention includes a kink-resistant catheter section containing at least an inner liner and a flexible outer member having a super-elastic alloy, ribbon braid located between the inner and outer members. The invention includes catheters comprising at least one such catheter section. The catheter section is configured so that it desirably has a critical bend diameter of no more than about 3 mm., preferably no more than 2 mm., and most preferably no more than 1 mm. Desirably, the catheter section self-recovers at least 95% of its original "straightness" after it has been subjected to kinking.

Figure 1:
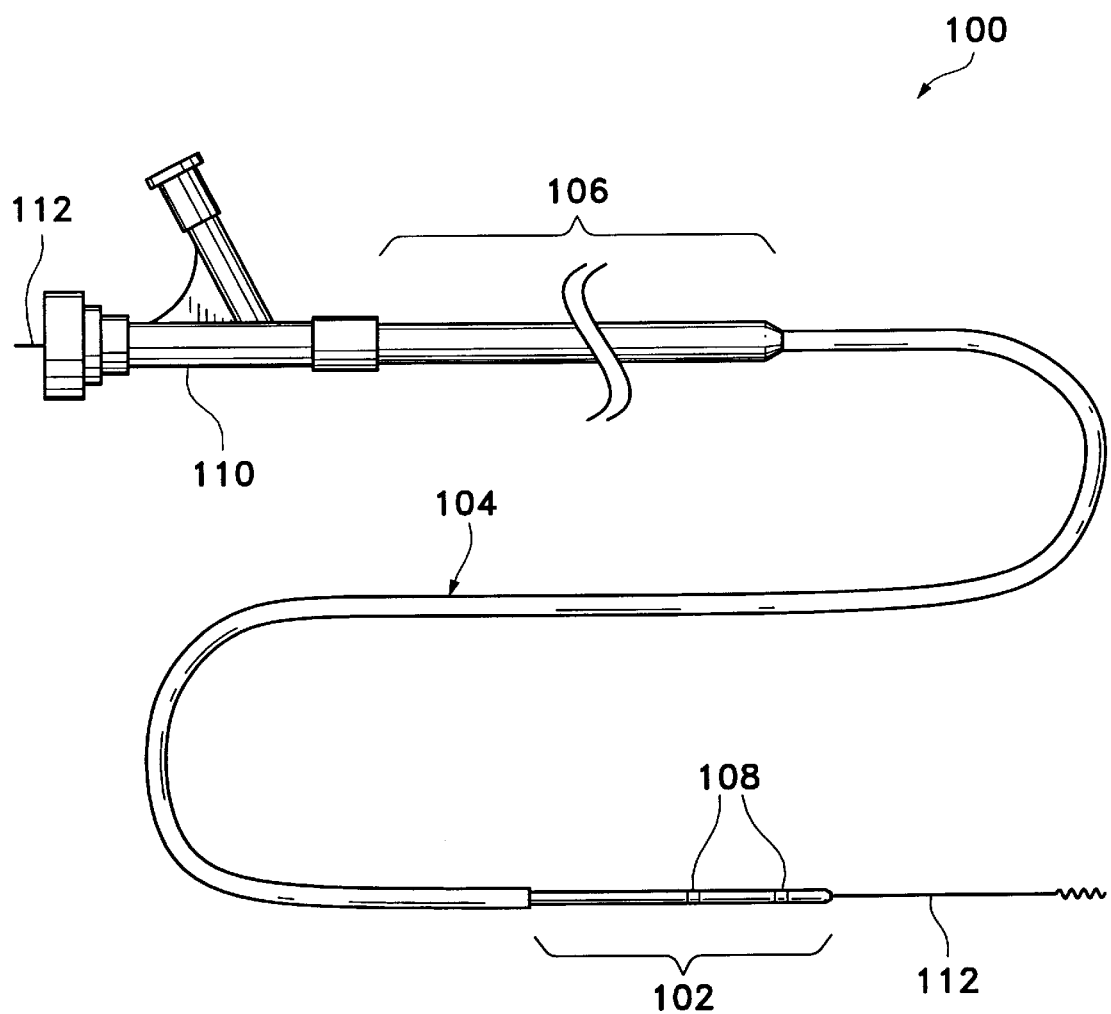
FIG. 1 shows, in side view, a typical three-section catheter made using the concepts of this invention.

A typical multi-section catheter (100) which may incorporate the concepts of this invention is shown in FIG. 1. Such a catheter is described in more detail in U.S. Pat. No. 4,739,768, to Engelson, (the entirety of which is incorporated by reference) and is particularly suitable for neurological and peripheral vascular applications. Clearly, then, it is also suitable for less demanding service such as might be encountered in access and treatment of the heart. One difficulty which has arisen as higher demands for length have been placed on these catheters is that the diameter of the distal section necessarily becomes smaller and smaller. This is so since the longer catheters must reach ever smaller vascular areas. This smaller diameter requires a concomitant thinning of the wall section. The thinner section walls may kink or ripple when actively pushed along the guidewire or when vaso-occlusive devices are pushed through the catheter's lumen. The typical configuration shown in FIG. 1 has a distal section (102) having significant flexibility, an intermediate section (104) which is typically less flexible, and a long proximal section (106) which in turn is least flexible.

The distal section (102) is flexible and soft to allow deep penetration of the extraordinary convolutions of the neurological vasculature without trauma. Various known and often necessary accessories to the catheter assembly, e.g., one or more radio-opaque bands (108) at the distal region to allow viewing of the position of the distal region under fluoroscopy and a luer assembly (110) for guidewire (112) and fluids access, are also shown in FIG. 1. The typical dimensions of this catheter are:

Overall length: 60–200 cm
Proximal Section (106): 60–150 cm
Intermediate Section (104): 20–50 cm
Distal Section (102): 2.5–30 cm Obviously, these dimensions are not particularly critical to this invention and are selected as a function of the malady treated and its site within the body. Typical of the catheters made using this invention are those in the 2 French to 5 French range. The inner diameter of such catheters is then 10 mils to 42 mils.

Furthermore, a catheter made using this inventive concept need not be of three sections increasing stiffness as is shown in FIG. 1. The catheter may be of two discrete sections or may be of four or more discrete sections of differing flexibility. Through judicious choice of physical parameters for the catheter sections, the components may also have varying physical parameters (e.g., lubricity, flexibility, wall thickness, inner or outer layer member composition, etc.) within the sections.

Typically, although not necessarily, when a three section catheter is desired, the most proximal section (106) is the "more proximal" or "stiff" section described herein. Again, although not necessarily, when a three section catheter is desired, the most distal section (102) is the "more distal" or "least stiff" section. The mid section (104) may be braided and referred to as "more distal" if the situation warrants it. It is a rare infusion catheter that utilizes a more distal section which is stiffer than any of its more proximal sections.

An additional benefit of the invention is that the use of the super-elastic alloy braid permits the walls of the catheter to be comparatively thinner with no diminution of performance, e.g., crush strength or flexibility, and may provide an improvement in performance.

Figure 2:
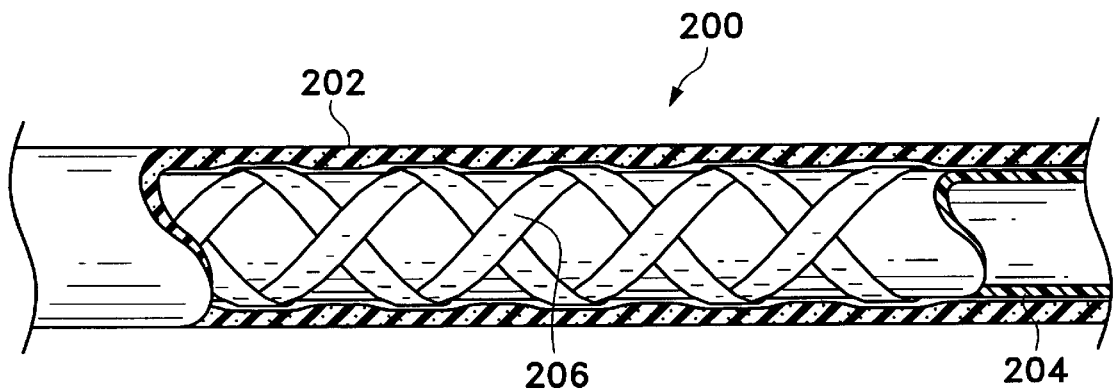
FIGS. 2, 3, 4, 5, and 6 show, in magnification, partial cross-sections of the inner portion of a catheter sections made using this invention.

FIG. 2 shows a magnified partial cross-section of a catheter body or section (200) showing the most basic aspects of one variation of this invention. As shown there, the catheter body section has an outer covering member (202) and an inner liner member (204). Situated between outer member (202) and inner member (204) is braid member (206). As shown in FIG. 2, both outer member (202) and inner member (204) are polymeric. They are desirably selected of materials which tack to each other upon heating. They may also be melt-miscible. In some instances, they may contain components which act in the manner of adhesives, but such is not necessary. Typically, for the simple variation shown in FIG. 2, the outer covering member (202) is of a material which is heat-shrinkable (e.g., low density polyethylene) or may otherwise be coated onto the structure (e.g., polyurethanes) onto the inner member (204) and the braid (206). Preferred polymeric materials for the inner liner include polyethylene, polypropylene, polyvinyl chloride (PVC), ethyl vinyl acetate (EVA), polyurethanes, polyamides, polyethylene terephthalate (PET), and their mixtures and copolymers. Preferred materials further include the lubricious polymers such as fluoropolymers such as polytetrafluoroethylene (PTFE or TFE), ethylene-chlorofluoroethylene (ECTFE), fluorinated ethylene propylene (FEP), polychlorotrifluoroethylene (PCTFE), polyvinylfluoride (PVF), or polyvinylidenefluoride (PVDF). Especially preferred is TFE.

We have found that when a fluorinated polymer is used as the inner tubing member, it is useful to etch the outside surface of the member to provide a good mechanical surface (with "tooth") to which the adjacent polymers will adhere. Certain procedures using, for instance, aliphatic hydrocarbons and sodium metal as the etching solution are known to be effective in such service.

Another useful class of polymers are thermoplastic elastomers, including those containing polyesters as components. Typical of this class is HYTREL. Additionally, an adhesive may be coated onto the outer surface of the inner liner tubing. Polyesters and polyimides, in particular, are suitable as adhesives.

An outer covering of polyethylene or of EVA or their mixtures, copolymers, etc. are excellent choices for the outer covering member. The polymer to be used as the outer covering is typically extruded into a tubing of appropriate size and thickness and then cross-linked to raise the melt temperature of the resulting tubing. The tubing is then inflated and perhaps stretched to give the included polymer a specific molecular orientation. The tubing, so treated, may then be slipped over the combination of inner liner (204) and braid (206) and heat shrunk into place.

A variety of other polymers may be used, depending upon the use to which the catheter section is placed. For instance, if the section (200) is used as a proximal section, the outer tubing may be a polyimide, polyamides (such as the Nylons), high density polyethylene (HDPE), polypropylene, polyvinylchloride, various fluorocarbon polymers (for instance: PTFE, FEP, vinylidene fluoride, their mixtures, alloys, copolymers, block copolymers, etc.), polysulfones, or the like. Blends, alloys, mixtures, copolymers and block copolymers of these materials are also suitable if desired.

If a more flexible section is required, the outer tubing member (202) may also be of a member selected from a more flexible material such as polyurethanes, low density polyethylene (LDPE), polyvinylchloride, THV, etc. and other polymers of suitable, softness or a modulus of elasticity.

FIG. 2 shows the results of either a heat-shrinking the outer tubing member (202) onto the assembly of inner liner tube (204) and braid (206). Contact regions between the outer covering member (202) and inner liner member (204) are shown in the interstices between the open weave of the braid (206). Although the open area between turns of the braid is not absolutely necessary as a means of allowing contact between the inner liner (204) and the outer covering (202), such is quite desirable. Furthermore, when the outer covering member (202) is placed on the outer surface of the catheter section (200) by dipping the inner assembly of braid (206) and inner member (204) into a molten or latex liquid, the contact is inevitable.

We have found that when using polyurethane as either the outer covering member (202) per se or as an inner portion of the outer covering member (202) (e.g., beneath a polyethylene layer), a suitable method for applying the polyurethane to the braid entails placement of a polyurethane tubing over the braid, placement of a polyethylene "shrink-wrappable" tubing over the polyurethane tubing, and heating the combination to pull the polyurethane down to the braid surface using the polyethylene tubing as the mover. The polyethylene may be removed or left in place.

The wall thickness of the outer tubing member (202) may be as thin as 0.5 mils. and as thick as 10 mils., depending upon catheter usage, section of the catheter chosen, polymer choice, and style of catheter.

Typically, a wall thickness of the inner liner (204) will be between 0.5 and 3.0 mils. These dimensions are obviously only ranges and each catheter variation must be carefully designed for the specific purpose to which it is placed.

Each of the polymers noted herein may be used in conjunction with radio-opaque filler materials such as barium sulfate, bismuth trioxide, bismuth carbonate, powdered tungsten, powdered tantalum, or the like so that the location of various portions of the catheter sections may be radiographically visualized within the human body.

As will be discussed below, it is within the scope of this invention to have multiple polymeric layers exterior of the braid (206) as well as multiple polymeric liner members interior to braid (206). Furthermore, it is within the scope of the invention to include multiple braids and/or flat ribbon coils between or amongst the various polymeric layers.

It is also within the scope of this invention to coat at least one of the exterior surface of outer member (202) and the inner surface of inner liner (204) with a lubricious layer, which either is chemically bonded to the layer or is physically coated on the relevant surface. A description of suitable procedures for producing such lubricious coatings is found at U.S. patent application Ser. Nos. 08/060,401 ("LUBRICIOUS CATHETERS"), filed May 12, 1993; 08/235,840 (METHOD FOR PRODUCING LUBRICIOUS CATHETERS"), filed Apr. 29, 1995; and 08/272,209 ("LUBRICIOUS FLOW DIRECTED CATHETER"), filed Jul. 8, 1994, the entirety of which are incorporated by notice. The metallic braid (206) shown in FIG. 2 is made up of a number of metallic ribbons. A majority of the metallic ribbons in braid (206) are of a member of a class of alloys known as super-elastic alloys.

Preferred super-elastic alloys include the class of titanium/nickel materials known as nitinol—alloys discovered by the U.S. Navy Ordnance Laboratory. These materials are discussed at length in U.S. Pat. Nos. 3,174,851 to Buehler et al., 3,351,463 to Rozner et al., and 3,753,700 to Harrison et al. Commercial alloys containing up to about 5% or up to about 8% or more, of one or more other members of the iron group, e.g., Fe, Cr, Co, are considered to be encompassed within the class of super-elastic Ni/Ti alloys suitable for this service. Most preferred are alloys containing 1.5–2.5% Cr and having a transition of less than 0 degrees C.

When using a super-elastic alloy, an additional step may be desirable to preserve the shape of the stiffening braid. For instance, with a Cr-containing Ni/Ti super-elastic alloy which has been rolled into a 1×4 mil ribbon and formed into a 16-member braid, some heat treatment is desirable. Braids which are not treated in this way may unravel during subsequent handling or may undertake changes in diameter or braid member spacing during that handling. In any event, the braid is placed onto a mandrel, usually metallic, of an appropriate size. The braid is then heated to a temperature of 650°–750° F. for a few minutes, possibly (but not necessarily) annealing the constituent ribbon. After heat treatment, the braid retains its shape and the alloy retains its super-elastic properties.

Metallic ribbons (202 and 206) that are suitable for use in this invention are desirably between 0.25 mil and 3.5 mil in thickness and 2.5 mil and 12.0 mil in width. By the term "ribbon", we intend to include elongated shapes, the cross-section of which are not square or round and may typically be rectangular, oval or semi-oval. They should have an aspect ratio of at least 0.5 (thickness/width). In any event, for super-elastic alloys, particularly nitinol, the thickness and width may be at the lower end of the range, e.g., down to 0.30 mil and 1.0 mil, respectively. Currently available ribbons include sizes of 0.75 mil×4 mil, 1 mil×3 mil, 1 mil×4 mil, 2 mil×6 mil, and 2 mil×8 mil.

The ribbons making up the braid (206) shown in FIG. 2 may also contain a minor amount of non-super-elastic alloy materials. Although metallic ribbons are preferred as the ancillary materials because of their strength-to-weight ratios, fibrous materials (both synthetic and natural) may also be used. Preferred, because of cost, strength, and ready availability are stainless steels (SS304, SS306, SS308, SS316, SS318, etc.) and tungsten alloys. In certain applications, particularly smaller diameter catheter sections, more malleable metals and alloys, e.g., gold, platinum, palladium, rhodium, etc. may be used. A platinum alloy with a few percent of tungsten is preferred partially because of its radio-opacity.

Suitable non-metallic ribbons include high performance materials such as those made of polyaramids (e.g., KEVLAR) and carbon fibers.

The braids utilized in this invention may be made using commercially available tubular braiders. The term "braid" is meant to include tubular constructions in which the ribbons making up the construction are woven radially in an in-and-out fashion as they cross to form a tubular member defining a single lumen. The braids may be made up of a suitable number of ribbons, typically six or more. Ease of production on a commercial braider typically results in braids having eight or sixteen ribbons.

The braid shown in FIG. 2 has a nominal pitch angle of 45°. Clearly the invention is not so limited. Other braid angles from 20° to 60° are also suitable. An important variation of this invention is the ability to vary the pitch angle of the braid either at the time the braid is woven or at the time the braid is included in the catheter section or sections.

Finally, the inner liner may be of a helically wound coil of wire or ribbon. The composition of the coil may be of any of the materials listed above for use in constructing the braid. The preferred materials for this metallic version of catheter section inner liner are the super-elastic alloys (especially the noted group of nitinols), stainless steels, and the radio-opaque metals and alloys (for instance, platinum alloys, especially platinum alloys with tungsten). These metallic liners may be made in the manner specified in detail in U.S. application No. 08/266,540 "Kink-Free Spiral Wound Catheter", filed Jun. 27, 1994 and in U.S. application No. 08/338,018 "High Performance Spiral Wound Catheter", filed Nov. 10, 1994, the entirety of which are incorporated by reference.

Figure 3:
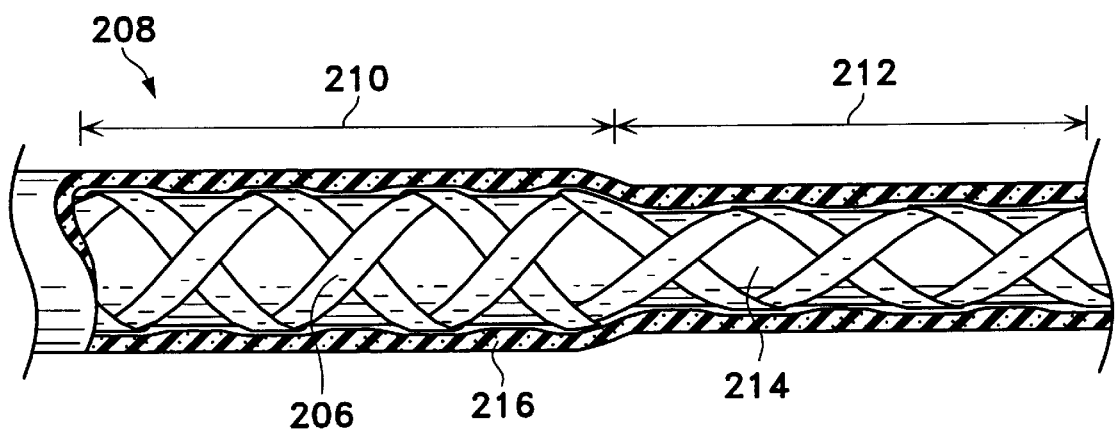

FIG. 3 shows a variation of the invention in which the braid (206) is used in a catheter section (208) having two portions of different diameter. The larger diameter portion (210) utilizes the braid with a nominal braid angle of 45 degrees and a smaller diameter portion (212) in which the same braid has a braid angle of 30 degrees. This diminution in catheter diameter may be accomplished in a number of different ways. For instance, inner liner (214) may be sized with two different diameters in the respected different portions (210 and 212) of the catheter section. The braid (206) may then be stretched axially as it is placed upon that liner. When the outer covering (216) is placed on the braid (206), the braid (206) will retain its multi-diameter configuration. This variation has the benefit of being quite simple in construction and yet provides a variety of different flexibilities to the catheter section without a significant change in the materials of construction.

Figure 4:
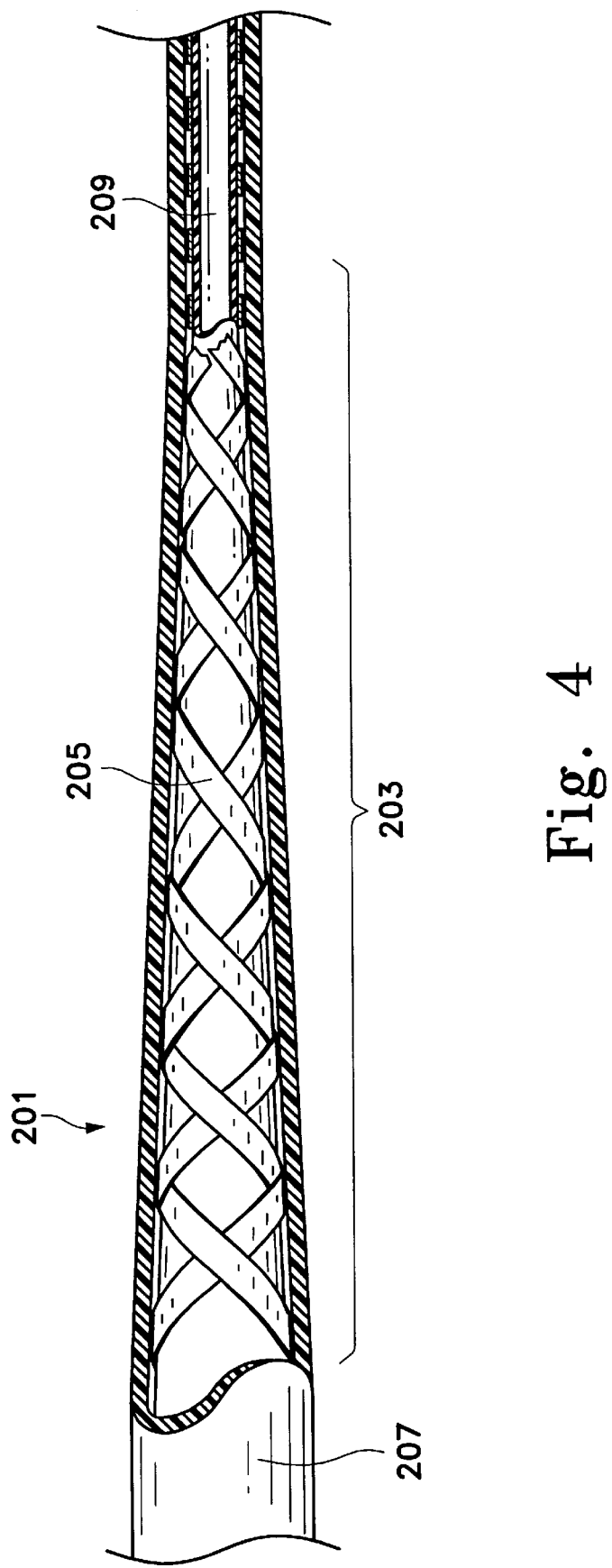

FIG. 4 shows a variation of the inventive catheter section (201) having a tapered section (203). The braid (205) changes its pitch from one end of the tapered section (203) to the other. Judicious choice of polymers allows a smooth transition from the larger adjacent section (207) to the smaller (typically) more distal section (209). The transition section (203) found in FIG. 4 is especially useful in catheters which are used to incorporate high flows of liquid material (when the catheter is used for treatment or diagnosis) or which are used for placement of vaso-occlusive devices (such as coils having inherent secondary structure as are found in U.S. Pat. No. 4,994,069, to Ritchart et al). The smooth transition allows the catheter to be used with ease due to the lower friction through the joint.

Figure 5:
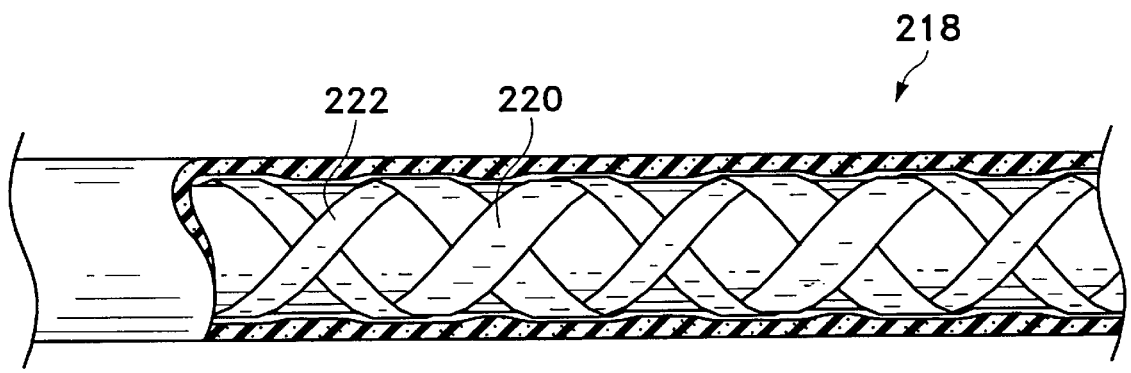

FIG. 5 shows another variation of the inventive catheter section (218) in which the braid is constructed of ribbons of different width. In this instance, the section (218) includes a braid having a wide ribbon (220) and a narrower ribbon (222). As noted above, it is desirable to balance the size and types of ribbons woven in each direction. As also noted above, these various ribbons should be, in the main, super-elastic alloy. However, they may be fibrous materials such as Kevlar or materials of other metals or alloys such as stainless steel. However, to accomplish the benefits of the invention, the major portion of the ribbons making up a braid should be super-elastic alloy.

Figure 6:
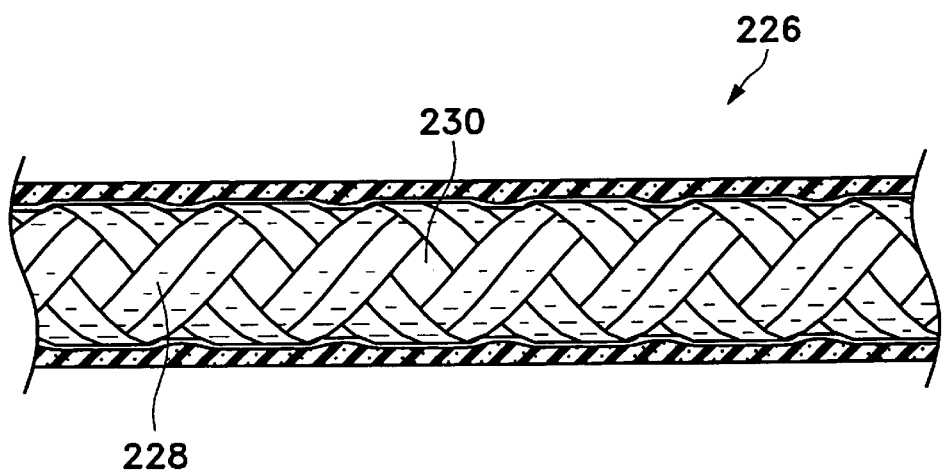

The variations shown above have each shown a single-ribbon wind. Single-ribbon winds permit the braid to contain the maximum amount of open area between ribbons in the braid. However, the catheter section need not be made with a single wind. FIG. 6 shows a variation of the inventive catheter section (226) in which the braid (228) was woven using a double-ribbon wind. In this variation, a pair of ribbons is placed side by side and treated as the single ribbon was in the variations described in FIGS. 2–5 above. This variation produces a braid which is denser than the single-ribbon wind. It is also thicker. Typically, the regions between adjacent winds are smaller. The invention described herein is intended to encompass multiple-wind braids. However, some of the benefits of the invention are diminished as the density of the ribbons in the catheter section is increased. That is to say that the stiffness of the catheter section substantially increases as the number of ribbons used in a multiple-ribbon weave is increased. The catheter sections shown in FIGS. 2, 3, 4, 5 and 6 may be combined in a variety of manners to produce a composite catheter assembly. As mentioned above, the typical vascular catheter is made up of a number of sections, typically each more flexible than the section more proximal.

Figure 7:
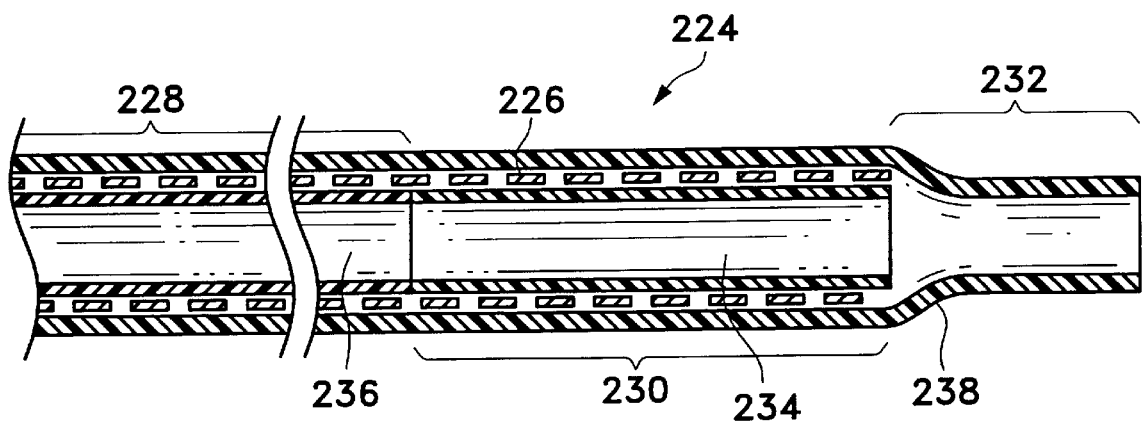
FIGS. 7, 8, 9, 10, 11, and 12 show, in magnified cross-section, various catheters having sections of differing stiffness.

FIGS. 7–13 show various ways to utilize the catheter sections of this invention in producing a catheter with sections of differing stiffness. In FIG. 7, catheter assembly (224) uses a single length of braid (226) extending from the proximal end of the catheter assembly (224) throughout the proximal section of the catheter (228) and throughout the midsection of the catheter (230). The distal section of the catheter (232) does not have braid (226) within. The difference in flexibility between proximal section (228) and midsection (230) lies in the fact that the inner liner members (234) in midsection (230) and inner liner (236) in proximal catheter section (228) are of differing moduli of elasticity. In this variation, the outer layer (238) is a single piece of shrink-wrap tubing, e.g., polyethylene, which extends both other the composite proximal end (228) and midsections (226). It extends to form the distal section as well. Such a catheter design would be one desirable in neurological use, that is, to reach into sites within the brain.

Figure 8:
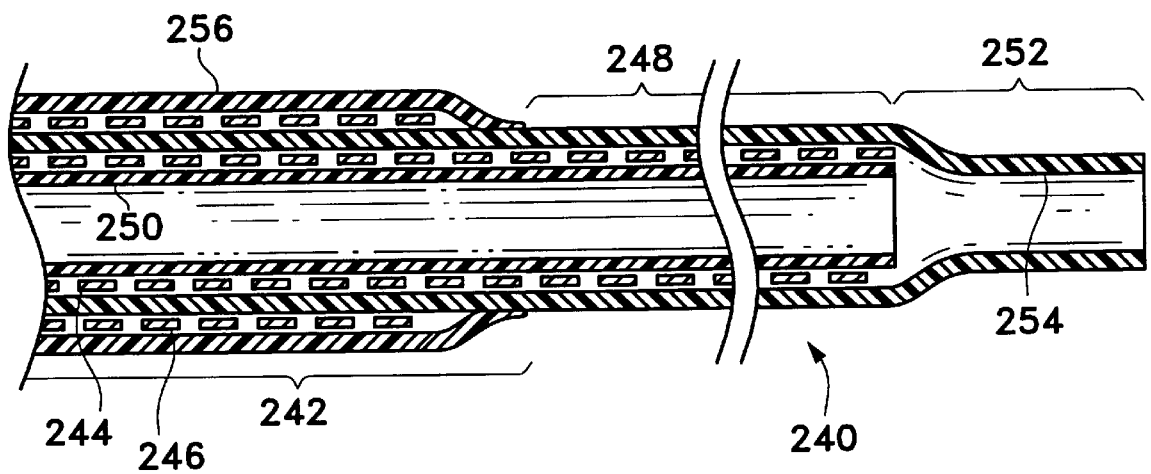

FIG. 8 shows another variation of a catheter assembly made using multiple layers of braided sections made according to the invention. This catheter assembly (240) uses a proximal section (242) made up of a number of layers but including an inner braid (244) and an outer braid (246). The inner braid (244) also extends down into and extends through the length of midsection (248). In this variation, the inner liner member (250) coextends, is coaxial with, and is internal to the inner braid (244). A middle layer of a polymeric tubing (254) extends from the proximal end of the catheter to the distal end of the catheter and forms the distal portion (252) of that catheter assembly. A further outer covering (256) covers braid (246).

Designs such as shown in FIG. 8 is one of exceptional stiffness in the proximal section (242). Although not critical for most neurological applications, such a catheter design has exceptional torque transmission. Such a catheter design may be desirable where a catheter is used for coronary or peripheral access.

Figure 9:
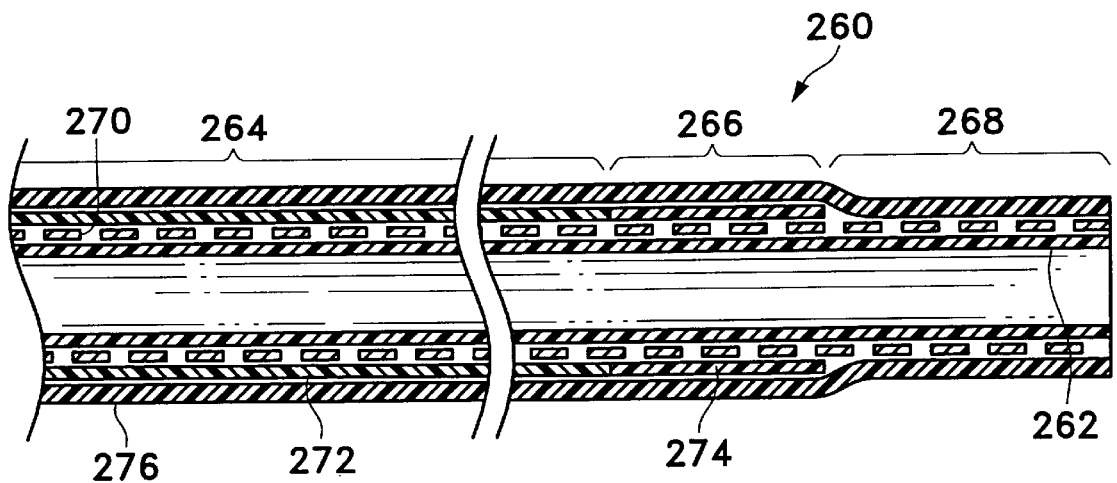

Another catheter design desirable for peripheral or coronary access is shown in FIG. 9. In this variation, catheter assembly (260) includes a tubing liner (262) which extends throughout the complete catheter assembly (260) from proximal section (264) through midsection (266) to distal section (268). More importantly, the braid (270) also coextends the length of inner liner (262). Differences in flexibility for the respective sections are provided by the use of polymeric tubing members (272) for the proximal section (264) and midsection tubing member (274) for the catheter assembly midsection (266). The absence of additional polymeric members other than the outer polymeric covering (276) renders distal section (268) the most flexible.

Figure 10:
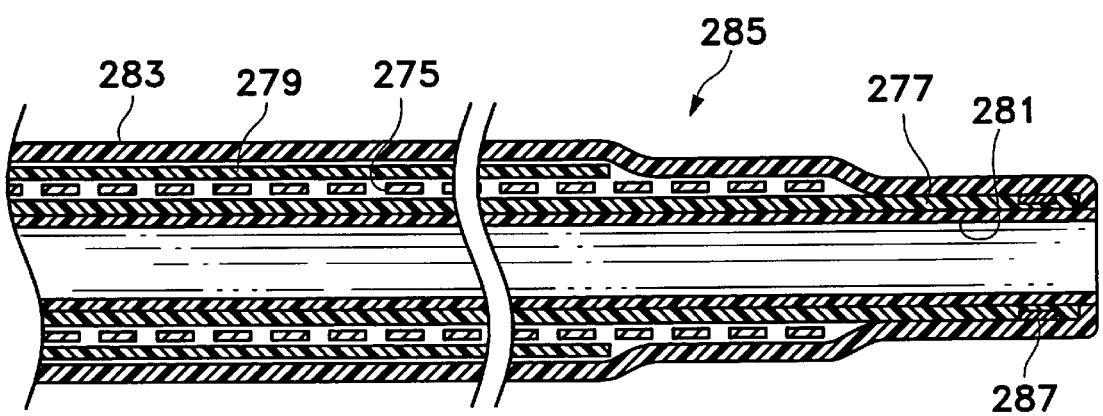

FIG. 10 shows a preferred variation of the invention in which the braided member (275) is surrounded by an inner polyurethane layer (277) and an upper polyurethane layer (279). The innermost layer (281) is a tubular member comprised of TFE which preferably has been etched (as discussed above) so to provide a good bond with the adjacent polyurethane layer. The outermost layer (283) is also made of a polyurethane. The section (285) also is shown with a radio-opaque band (287) in the distal end. In such a variation, the various polyurethanes vary in hardness according to their position on the section. For instance, the outermost layer (283) and the upper layer (279) might be one having a Shore 75A–85A hardness; the inner layer (277) might be a Shore 55D polyurethane or the like. Various spacers and adhesives have been omitted from the depiction of the variations to simplify those drawings.

Figure 11:
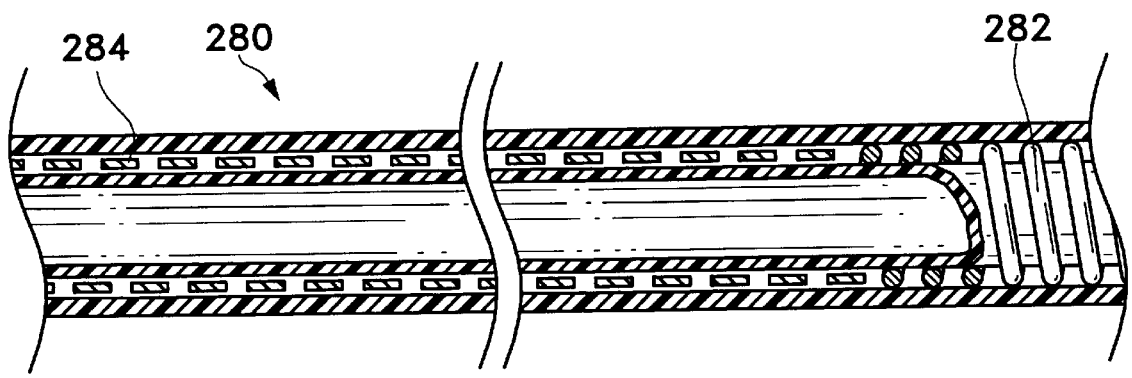
Figure 12:
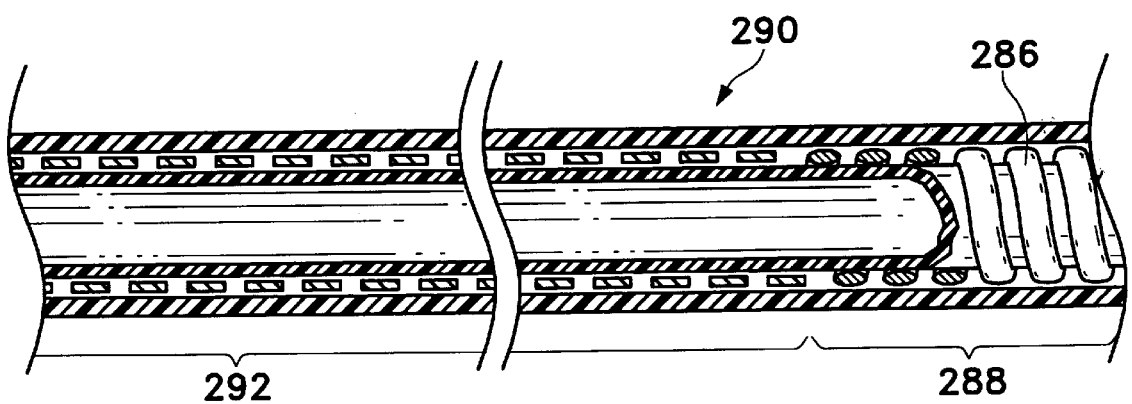

FIGS. 11 and 12 show cross-sectional, partial cutaways of catheter assemblies utilizing braided catheter sections joined to more distal catheter sections made in other ways. In the variation shown in FIG. 11, a coil (282) is placed in the more distal portion of the catheter assembly. It abuts the single-layer of braid (284) axially. Similarly, in FIG. 12, a ribbon (286) is used in the distal portion (288) of catheter assembly (290). The braid is used only in the remaining portion of the catheter assembly (290).

Figure 13:
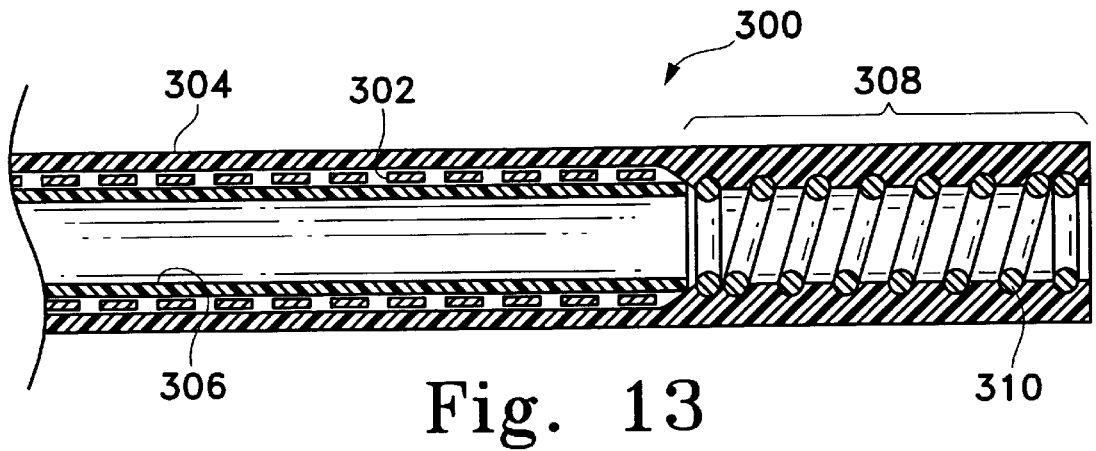
FIGS. 13, 14, and 15 show, in magnified cross-section, various distal end sections of catheters.
Figure 14:
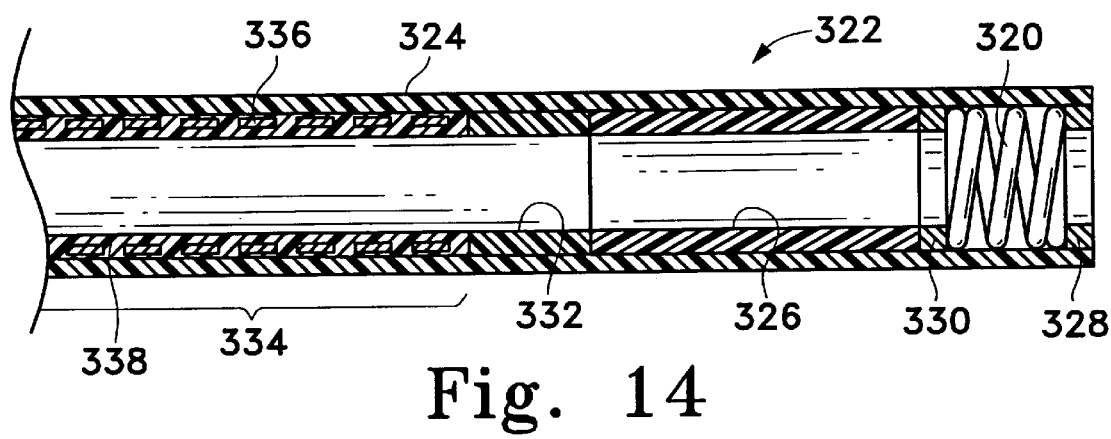

FIGS. 13 and 14 depict other embodiments of the invention in which various distal sections are integrated into a section of a catheter having a braid member as is discussed above. For instance, FIG. 13 shows a variation (300) of the invention in which the braid (302) is sandwiched between two polymeric layers, the outer layer (304) and the inner layer (306). Distal to the braided section is a section (308) having an interior surface feature comprising a hard or lubricious polymeric strand (310) helically wound to provide a contact surface for guidewires and the like as they pass through the distal catheter lumen. The helically wound interior strand (310) may be embedded into the exterior polymer (304) or otherwise adhered to the catheter distal portion. It is preferable to embed more than about half of the strand (310) into the surrounding polymer (304) so to prevent that resulting surface from catching the guidewires and other devices during their passage. A highly preferred polymer for the strand (310) is polytetrafluoroethylene and other similar polymers.

FIG. 14 shows another variation of the inventive catheter using a largely polymeric tip section but configured to resist kinking in a way different than that found in conjunction with the braid reinforced catheter section.

FIG. 14 shows a distal section having a single radio-opaque marker (302). The presence of a comparatively inflexible radio-opaque marker in the typical extremely flexible distal section represents an exceptional challenges in producing a kink-resistant tube. The challenge is especially acute when the two-marker variation is considered. Under high flexure, the region just adjacent the markers is likely to kink and then bind upon advancement of the relatively rigid vaso-occlusive devices, particularly when the diameter of the vaso-occlusive device is close in size to the inner diameter of the open lumen. The use of a single layer of a polymer (often a polyethylene shrinkable tubing) which is flexible enough to function effectively as a distal section for tracking through the cerebral vasculature often is insufficiently strong to maintain its interior shape in the critical region near the radio-opaque markers. Increasing the thickness of the layer to alleviate the kinking problem raises the stiffness of the section often to marginally unacceptable levels. By combining two layers of closely matched tubing materials in an overall thickness typically no greater than the thickness of the marker, the dual goals of enhanced kink-resistance and acceptable flexibility may be met especially when the abuts the marker rather than over- or under-lapping the marker.

FIG. 14 shows a distal section (322) having a single distal radio-opaque marker (320). In this instance, the single radio-opaque marker (320) is shown to be a coil although the marker may be a band. In this variation, the outer tubing (324) and the marker may be strengthened in this region of the catheter by the introduction of the thin inner stiffener layer (326). Also shown are a variety of spacer sections used to hold various components in place during assembly and to maintain those position during later use. These sections are the distal radio-opaque coil marker spacers (328 and 330) and the transition spacer (332) between the distal section of the catheter and the midsection (334) containing the braid member (336). The inner liner (338) in that midsection (334) is also shown. In some instances, it may not be necessary to utilize an independent midsection but instead a single proximal section may abut the transition spacer (332).

Although the outer layer (324) may be of a wide variety of materials such as polyurethanes, polyvinyl chloride, LDPE, LLDPE, the outer layer (324) is desirably a shrinkable tubing having an EVA content of at least 7–10% EVA, preferably 12–20% and a wall thickness of 0.0005 to 0.010", preferably about 0.003". The inner liner (326) preferably is a similar composition but with a lower (or, preferably, no) EVA. Specifically, the preferred material is LLDPE or LDPE. The wall thickness of such tubing may be 0.0005 to 0.0020", preferably about 0.0015".

The stiffness of this combination of materials typically produces a lateral stiffness measured as an axial deflection force of no more than about 3.0 gm, preferably no more than about 2.2 gm. This stiffness is measured by placing a 3 cm. length of the section in a position normal or directly perpendicular to a plate connected to a meter capable of measuring force against the plate. The section is moved directly perpendicular to the measuring plate and the force measured. The measured force typically increases to a plateau as the section bends against the measuring plate. The value of that measured plateau is value used in assessing the stiffness of the catheter section.

Additionally, this catheter section exhibits comparatively high performance kink resistance, e.g., the catheter section has a critical bend diameter of no more than about 6.0 mm, preferably no more about 4.0 mm.

It should be apparent that the outer layer (324) may also be applied by dipping the inner tubing layer (326) into a molten polymer bath or into a polymer dissolved in a solid or into a suspension or latex comprising the outer cover polymer. Obviously, the cover may be placed on the catheter by spraying or otherwise applying the material. Included in such a class are the polyurethanes, polysilicones, polyvinylpyrrolidone, etc.

The catheter section (322) may be coated or otherwise treated both inside and outside to increase their lubricity.

The distal catheter section (322) noted in FIG. 14 is especially suitable for use with the kink-resistant sections comprising braided members discussed above in those instances in which a metal containing distal tip is not optimum.

Figure 15:
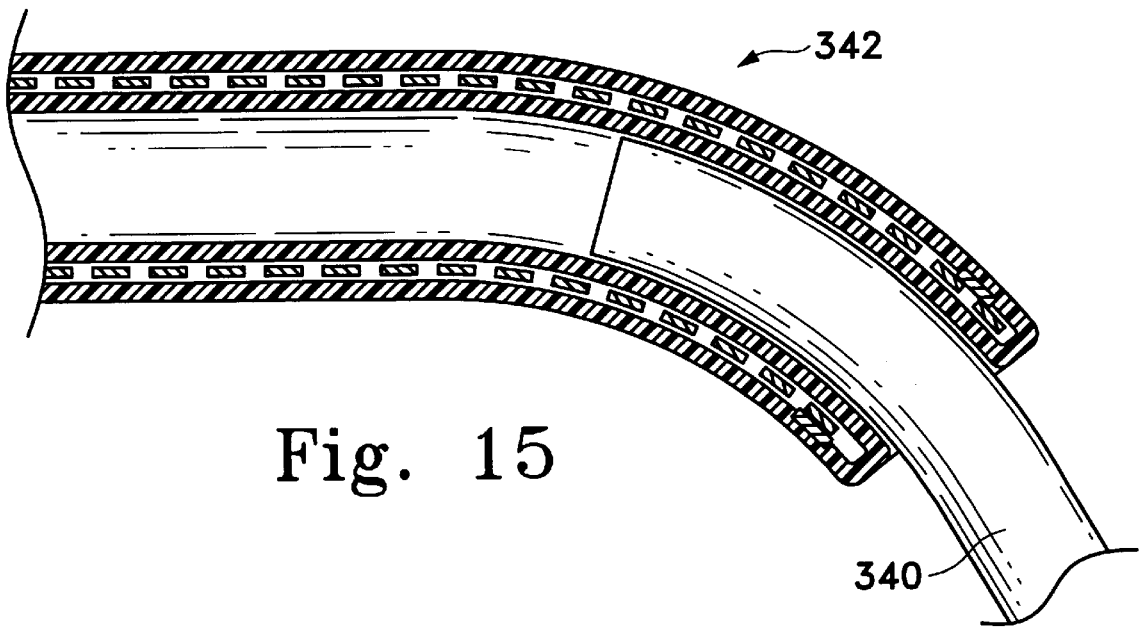

FIG. 15 shows the use of a shaping mandrel in forming one of the distal tips (342) discussed above. It should be understood that although the majority of the preferred embodiments of the invention are both quite kink-resistant and quite flexible, it is within the purview of the generic concept of this invention that the distal tip of the catheter may be given, a non-linear "pre-shape" sufficient to aid the movement of the catheter through the vasculature. The use of mandrel (340) also produces a very smooth inner surface in the catheter approximating the finish of the mandrel itself. Occasionally, the designer will need add a layer of polymer to enhance the stiffness of the section to allow maintenance of the tip shape during use.

Figure 16:
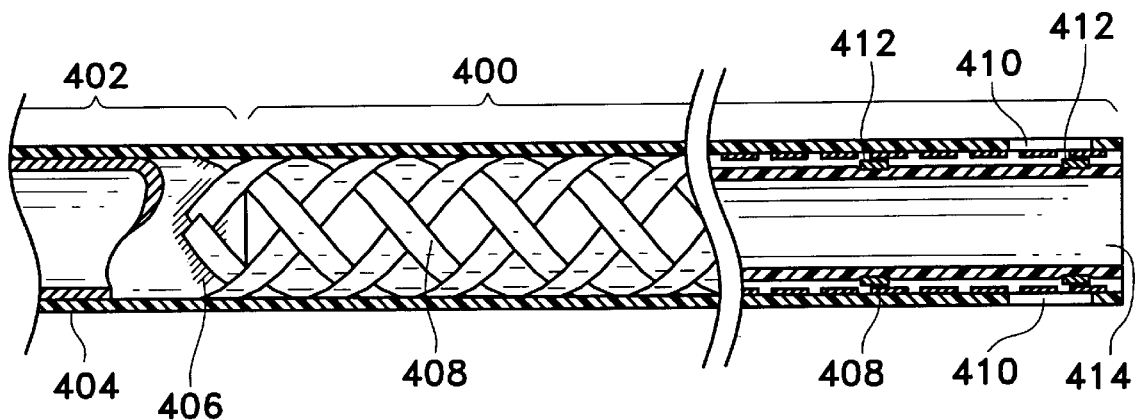
FIG. 16 shows, in magnification, partial cross-sections of the inner portion of a catheter section using this invention.

The catheter sections of this invention may be used in conjunction with other catheter portions which are more proximal to the individual sections discussed above. FIG. 16, for instance, depicts, in partial cross section, a typical joint as might be found between a more-proximal section comprising metallic tubing and a braided more-distal section. In this instance, the more distal-section of the invention is adjacent the more-proximal catheter section of the invention. In particular, the braid (408) in the more-distal section (400) is soldered or welded or otherwise attached to the more-proximal segment (402). An outer covering (404) such as has been discussed above may be applied to the outer surface of both the more-distal section (400) and the more-proximal segment (402). The outer covering (404) may be a material of suitable flexibility and compatibility such as a polyurethane or low density polyethylene and obviously may be covered or coated with a lubricious polymeric material such as a hydrophilic polymer material, e.g., one containing polyvinylpyrrolidone. The more-distal catheter section (400), as well as the stiffer more-proximal section, may include a lubricious inner layer (not shown), e.g., a Teflon or similar, as has been discussed above.

In the variation of this invention shown in FIG. 11, the use of metallic more-proximal sections (402) and metallic braids (408) in the more-distal section (404) and their junction via, e.g., a solder junction at (406), creates an electrical pathway for use with any of a variety of electrically impelled devices. One use of special interest is as the delivery catheter in the deployment of the vaso-occlusive device described in U.S. Pat. Nos. 5,122,136 and 5,354,295, to Guglielmi and Sepetka. Further variations of the concept are found in U.S. patent application Ser. No. 08/430,744 by Mills, filed Apr. 28, 1995 entitled "Delivery Catheter for Electrolytically Detachable Implant" and (Attorney Docket 29025-20132.00) by Sheldrup, filed Jul. 7, 1995 entitled "RF Occlusion Device and Method". The entirety of each is incorporated by reference. These devices operate in the following manner: a vaso-occlusive device which is attached to the end of a conductive core wire (via a sacrificial joint) is passed through the vasculature until a desired site is reached. The vaso-occlusive device is at (or in) the desired site; the sacrificial joint is in contact with the local body fluid or a conductive fluid, e.g., saline solution, introduced through the catheter. A small electric current is then passed through the core wire, perhaps with a superimposed RF component. A current is passed through the core wire with the expectation that the current will cause the sacrificial joint between the vaso-occlusive device and the distal tip of the core wire to electrolytically dissolve or disintegrate thereby freeing the vaso-occlusive device. In the two Guglielmi et al patents, the current "return" circuit is formed through the blood and thence to a skin patch attached to the current supply source. The Mills catheter uses the catheter as a return leg of the electrical circuit used to electrolytically dissolve the sacrificial link to the vaso-occlusive device.

The catheter assembly shown in FIG. 16 is used in such a system as the "return" conductor much in the same way as is the conductor in Mills catheter. Specifically, FIG. 16 shows at the distal-most portion of the section (400) a series of small ports (410) through outer wall covering (404). These small ports (410) are often no more than about 0.006" in diameter but allow access of the body fluid to the metallic braid (408) to form a portion of the circuit. Also shown are two radio-opaque bands (412), of e.g., platinum, to allow more certain visualization of the catheter tip during the procedure. Although the inner liner is not required in all procedures using this catheter assembly, when a vaso-occlusive device such as those described in the Guglielmi et al, Scheldrup, and Mills documents is used, the liner is highly desirable as an insulator so to isolate the core wire electrically from the metallic braid and further to isolate the electrolytic or electrical activity at the sacrificial joint.

It should be noted that in situations such as described above in which the braid (4308) is used as a conductor, it may be desirable to include a better conductor, e.g., gold, silver, copper, platinum, as one or more of the ribbons making up the braid. Similarly, the super-elastic alloy ribbons may be plated with such a conductor so to improve the conductivity of the braid/metallic tube assembly.

Again, it should be emphasized that the use of the open ports (410) and the overall conductivity of the assembly is not necessary to this variation of the invention. The metallic more-proximal section (402) may be used simply as a stiff proximal portion if the designer so desires.

Figure 17:
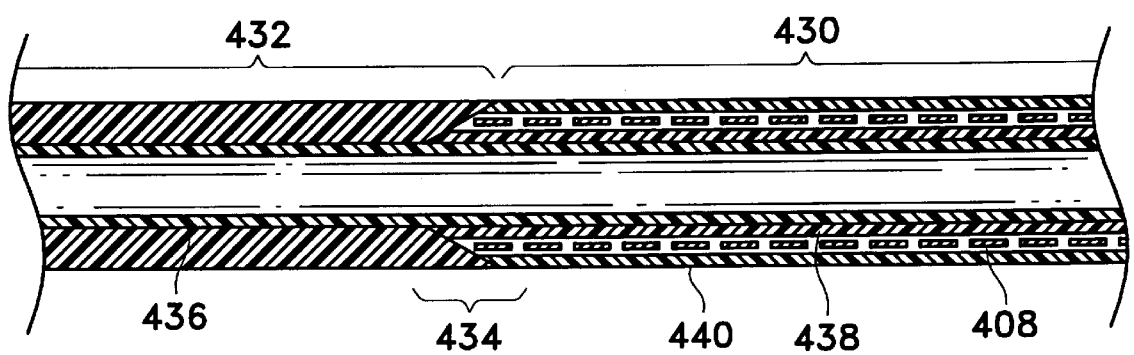
FIG. 17 show, in magnified cross-section, a catheter having sections of differing stiffness.

FIG. 17 depicts in partial cross-section another variation of the invention in which a more-distal segment (430) is attached to the more-proximal segment (432) via a conical or scarfjoint (434). In this variation the depicted sections have a common lubricious inner layer (436), e.g., a Teflon or similar, as has been discussed above. This inner layer (436) is optional and need not be found in each such segment. Nevertheless, the inner layer provides a for a number of benefits: it may form the cover for a mandrel upon which the adjacent layer (438) and then upon which the braid (408) may be wound or braided. As noted, the inner layer may be omitted, particularly in the more proximal region (432) since the majority of materials which are suitable for the more proximal section are very "hard" and suitably slippery for passage of guidewires and the like. The more-proximal section (432) may be a simple tubular member comprising unfilled, filled, or fiber-reinforced, tough, polymeric materials preferably having high flexural moduli. Examples generically include polyamides (Nylons 6, 66, 69, 610, 612, 46, 11, and aromatic polyamides such as supplied by DuPont, Huls, etc.), polyamide-polyimides (such as those supplied by Amoco Performance Products), polyimides (both thermoset and thermoplastic), polycarbonates, LCP's, acetals (such as Delrin), and (preferably) stiffer polyolefins such as polypropylene or high density polyethylene, etc.

To integrate the more proximal region (432) of the catheter assembly with materials found in adjacent regions, the choice of materials for the proximal section is desirably a polyamide which is melt-miscible with a polymeric component found in the next more distal segment. In this preferred instance, the more distal region (430) may(for instance) have a covering (440) of polyurethane, a block copolymer of a polyether and a polyamide (e.g., a Pebax), or a low durometer Nylon. Such polymers are melt miscible with the Nylon of the more distal section (432). The outer covering (440) and the more distal section (432) may be covered or coated with a lubricious polymeric material such as a hydrophilic polymer material. It is also highly desirable to choose a translucent or transparent polymer for this section to assist the physician in use of the catheter assembly.

Again, it should be noted that although the exemplified catheter assemblies in the Figures utilize only two or three sections, this invention is not so limited. The number of sections is selected by the designer when conceptualizing a specific use for a chosen device. Often, the optimum number of sections ends up being three simply because of the physiology of the human body, however, three or more may be involved in this invention. The sections additionally need not be of constant stiffness. They may also vary in stiffness—typically as the distal end of a section is approached, the section becomes more flexible.

Figure 18A:
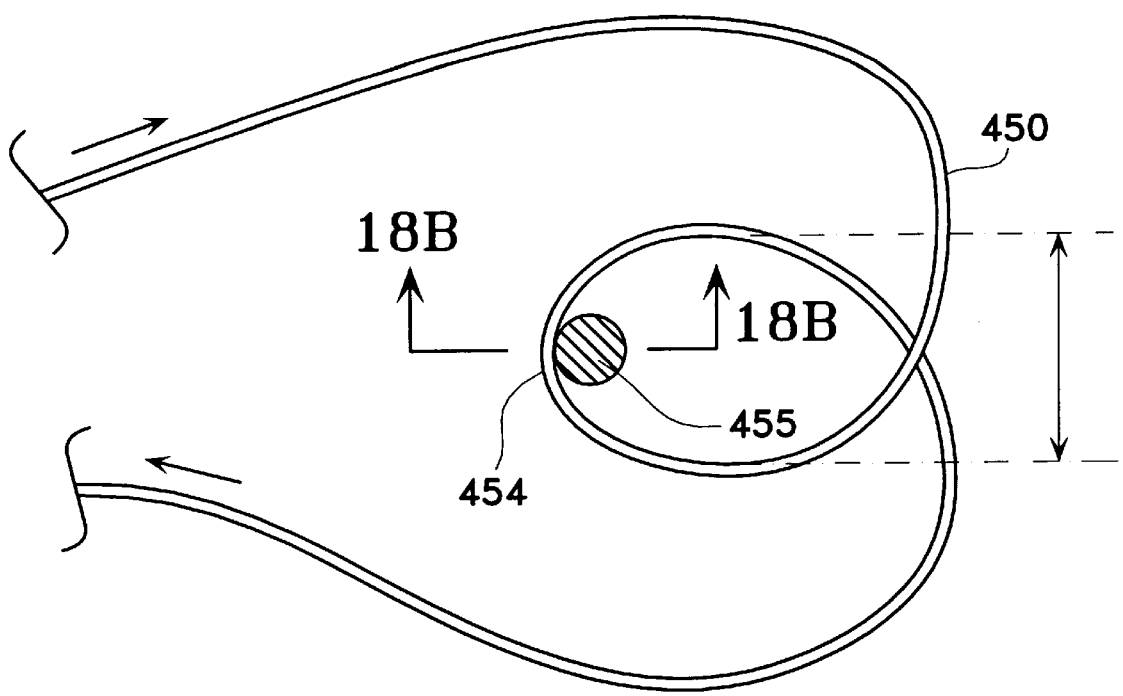
FIGS. 18A and 18B show details of a method for determining "critical bend diameter" for a catheter section.
Figure 18B:
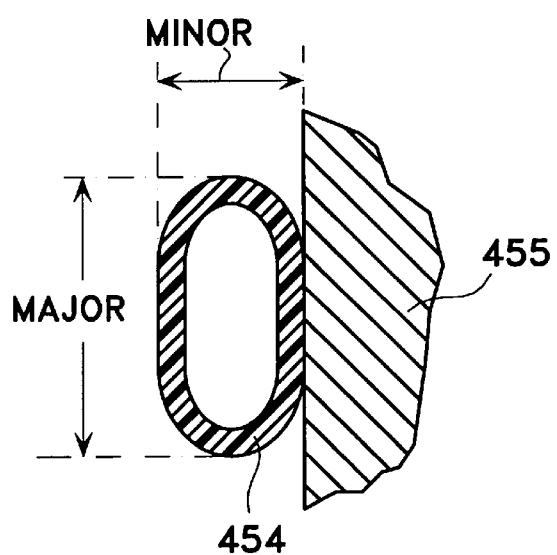

One test we utilize for critical bend diameter determination is shown schematically in FIGS. 18A and 18B.

In general, as shown in FIG. 18A, a catheter section (450) is placed between two plates (desirably of plastic or glass or the like for visibility) and often with an optional peg (455) to hold the catheter section loop (454) in place. The ends of the catheter are then pulled until a kink appears in the body of the catheter the critical bend diameter is the length of the arrow in FIG. 18A at the appearance of that kink. Alternatively, the ratio of the outer diameters (major diameter:minor diameter) as measured at apex (454) reaches a value of 1.5. FIG. 18B shows the cross section of the catheter sector at (454) against the peg (455) and further shows the manner in which the major diameter and the minor diameter are measured. These two methods provide comparable results although the latter method is more repeatable.

Many times herein, We refer to the "region" section of the catheter. Where the context permits, by "region" we mean within 15% of the point specified. For instance, "the distal region of the distal section" would refer to the most distal 15% in length of the distal section.

EXAMPLE 1

We constructed a catheter having three regions of differing flexibility. The most distal region was the most flexible. The catheter was completely lined from proximal end to distal end. The braid extended from proximal end to distal end. The braid was woven from eight ribbons of a commercial nitinol alloy containing about 2% Cr (sold by Shape Memory Applications Co. of Santa Clara, Calif.). The alloy had a thermal transition temperature (between austenitic and martensitic phases) of −10° C. The braid was placed on a 0.024" diameter stainless steel mandrel and heat-treated at 650–700° F. for 15–30 minutes to permit the braid to maintain its shape. A liner of a PTFE/FEP blend tubing was placed within the braid. The proximal section was covered with a tubing of Shore 72D polyurethane; the midsection was covered with a tubing of Shore 60D polyurethane; the distal section was covered with a tubing of Shore 85A polyurethane. The polyurethane tubing members were of a commercial resin sold under the CARBOTHANE trademark. The resulting had a 0.038" O.D. The distal section had a critical bending diameter of 3 mm.

EXAMPLE 2

We constructed a second catheter also having three regions of differing flexibility of the same polymers as the catheter in Example 1. The most distal region was the most flexible. In this instance, the catheter was completely lined from proximal end to distal end with a nitinol ribbon coil. The ribbon was a 1 mil by 6 mil nitinol ribbon which was tightly wound, i.e., with substantially no space between adjacent turns. The braid extended from proximal end to distal end axially between the ribbon coil and the polymeric outer covering. The braid was again woven from eight ribbons of the alloy mentioned in Example 1. The outer covering was of the same composition as the Example 1 catheter. The resulting catheter had a 0.038" O.D. The distal section appeared to have a critical bending diameter of 2.5 mm.

This invention has been described and specific examples of the invention have portrayed. The use of those specifics is not intended to limit the invention in any way. Additionally, to the extent that there are variations of the invention which are within the spirit of the disclosure and yet are equivalent to the inventions found in the claims, it is our intent that those claims cover those variations as well.

We claim as our invention:

1. A catheter section comprising:
   an elongate tubular member having a proximal end and a distal end and a passageway defining an inner lumen extending between those ends, comprising
   a.) a braid member woven of a plurality of ribbons, at least a majority of which ribbons comprise a superelastic alloy, and having inner and outer surfaces, and which said braid member extends along at least a portion of said lumen,
   b.) at least one polymeric inner lining member interior to said braid member, and
   c.) at least one outer covering member exterior to said braid member, said outer covering member comprising a first section and a second section, each section comprising a different material.

2. The catheter section of claim 1 wherein the catheter section has a critical bend diameter of no more than 3.0 mm.

3. The catheter section of claim 1 wherein the catheter section has a critical bend diameter of no more than 2.0 mm.

4. The catheter section of claim 1 wherein the catheter section has a critical bend diameter of no more than 1.0 mm.

5. The catheter section of claim 1 wherein the polymers are selected from members selected from the group consisting of polyimides, polyamides, polyesters, polyethylene, polypropylene, polyvinylchloride, polyfluorocarbons, polyurethanes, polysulfones, and their mixtures, alloys, blends, copolymers, and block copolymers.

6. The catheter section of claim 5 wherein said at least one polymeric inner lining member interior to said braid member comprises a polyfluorocarbon.

7. The catheter section of claim 6 wherein said at least one polymeric inner lining member interior to said braid member comprises polytetrafluoroethylene.

8. The catheter section of claim 7 wherein the section has a distal end and a proximal end and said polytetrafluoroethylene extends between said distal and proximal end.

9. The catheter section of claim 1 wherein the super-elastic alloy comprises a nickel-titanium alloy.

10. The catheter section of claim 1 wherein the super-elastic alloy comprises a nickel-titanium alloy further containing an alloying member selected from the group consisting of vanadium, chromium, manganese, iron, and cobalt.

11. The catheter section of claim 10 wherein the alloying member is selected from the group consisting of chromium and iron.

12. The catheter section of claim 1 wherein a minority of the braid member ribbons comprise stainless steel.

13. The catheter section of claim 1 wherein a minority of the braid member ribbons comprise a member selected from the group consisting of platinum, tungsten, gold, and their mixtures and alloys.

14. The catheter section of claim, 1 wherein a minority of the braid member ribbons comprise a polymer.

15. The catheter section of claim 1 wherein a minority of the braid member ribbons comprise carbon fiber.

16. The catheter section of claim 1 wherein the inner liner and outer covering members are radiation sterilizable without substantial degradation of physical attributes.

17. The catheter section of claim 1 wherein the braid member has a braid pitch and that braid pitch is constant along the axis of the braid member.

18. The catheter section of claim 1 wherein the braid member has a braid pitch and that braid pitch is not constant along the axis of the braid member.

19. The catheter section of claim 1 where the braid member ribbons have a thickness between 0.5 mil and 3.5 mil and a width between 2.5 and 12.0 mil.

20. The catheter section of claim 1 further comprising more than one braid member located coaxially with respect to each other.

21. The catheter section of claim 1 further comprising a removable, slidable guidewire placed interior to and in slidable relationship to said section.

22. A catheter comprising:
an elongate tubular member having a proximal end and a distal end and a passageway defining an inner lumen extending between those ends,
said elongate tubular member having:
a.) a relatively flexible more-distal segment comprising an elongate tubular member having a proximal end and a distal end and a passageway defining an inner lumen extending between those ends, comprising
 i.) a braid member woven of a plurality of ribbons, at least a majority of which ribbons comprise a super-elastic alloy, and having inner and outer surfaces,
 ii.) at least one inner polymeric lining member interior to said braid member, and
 iii.) at least one distal outer covering member exterior to said braid member, and
b.) a relatively stiff more-proximal segment comprising an elongate tubular member having a proximal end and a distal end and a passageway defining an inner lumen extending between those ends, comprising
 i.) said braid member extending from the more distal segment into the more proximal segment,
 ii.) said inner polymeric lining member extending from the more distal segment into the more proximal segment, and
 iii.) at least one proximal outer covering member exterior to said braid member, the proximal outer covering member comprising a material different than the material of at least a portion of the distal outer covering member.

23. The catheter of claim 22 wherein the catheter section has a critical bend diameter of no more than 2.0 mm.

24. The catheter of claim 22 wherein the catheter section has a critical bend diameter of no more than 1.0 mm.

25. The catheter of claim 22 wherein at least one of said at least one outer covering members comprise a polymer.

26. The catheter of claim 25 wherein the polymers are selected from members selected from the group consisting of polyimides, polyamides, polyesters, polyethylene, polypropylene, polyvinylchloride, polyfluorocarbons, polyurethanes, polysulfones, and their mixtures, alloys, blends, copolymers, and block copolymers.

27. The catheter of claim 22 wherein the super-elastic alloy comprises a nickel-titanium alloy.

28. The catheter of claim 22 wherein the super-elastic alloy comprises a nickel-titanium alloy further containing an alloying member selected from the group consisting of vanadium, chromium, manganese, iron, and cobalt.

29. The catheter of claim 22 wherein said at least one polymeric inner lining member interior to said braid member comprises a polyfluorocarbon.

30. The catheter of claim 29 wherein said at least one polymeric inner lining member interior to said braid member comprises polytetrafluoroethylene.

31. The catheter of claim 22 wherein a minority of the braid member ribbons comprise a member selected from platinum, tungsten, gold, their mixtures and alloys.

32. The catheter of claim 22 wherein the braid member has a braid pitch and that braid pitch is constant along the axis of the braid member.

33. The catheter of claim 22 wherein the braid member has a braid pitch and that braid pitch is not constant along the axis of the braid member.

34. The catheter section of claim 1 wherein one of said sections of the outer covering comprises a polyether based polymer.

35. The catheter of claim 22 wherein at least a portion of the distal outer covering member comprises a polyether based polymer.

* * * * *

UNITED STATES PATENT AND TRADEMARK OFFICE

CERTIFICATE OF CORRECTION

PATENT NO. : 6,143,013

DATED : November 7, 2000

INVENTOR(S) : Gene SAMSON et al.

It is certified that error appears in the above-identified patent and that said Letters Patent is hereby corrected as shown below:

In claim 14, please replace "claim, 1" with --claim 1--.

Signed and Sealed this

Eighth Day of May, 2001

Attest:

NICHOLAS P. GODICI

Attesting Officer        Acting Director of the United States Patent and Trademark Office